United States Patent [19]

Klinge et al.

[11] Patent Number: 5,693,637
[45] Date of Patent: Dec. 2, 1997

[54] BICYCLE DERIVATIVES, THEIR PREPARATION AND USE

[75] Inventors: Dagmar Klinge, Heidelberg; Liliane Unger, Ludwigshafen; Manfred Raschack, Weisenheim; Wolfgang Wernet, Hassloch, all of Germany

[73] Assignee: BASF Aktiengesellschaft, Ludwigshafen, Germany

[21] Appl. No.: 656,246

[22] PCT Filed: Nov. 30, 1994

[86] PCT No.: PCT/EP94/03980

§ 371 Date: Jun. 6, 1996

§ 102(e) Date: Jun. 6, 1996

[87] PCT Pub. No.: WO95/15963

PCT Pub. Date: Jun. 15, 1995

[30] Foreign Application Priority Data

Dec. 7, 1993 [DE] Germany .................... 43 41 665.9

[51] Int. Cl.[6] ............ A61K 31/55; A61K 31/505; C07D 487/04; C07D 471/04
[52] U.S. Cl. ............ 514/221; 514/258; 544/279; 544/285; 540/502; 540/506
[58] Field of Search .................. 540/502, 506; 544/279, 285; 514/221, 258

[56] References Cited

U.S. PATENT DOCUMENTS 5,403,836  4/1995  Blackburn et al. .............. 340/506

FOREIGN PATENT DOCUMENTS 456 835  11/1991  European Pat. Off. .

OTHER PUBLICATIONS

JAMA, Dec. 12, 1990–vol. 264, No. 22.

J. Vascular Med. Bio. 2, 207, 1990.

Biochemical and Biophy. Res. Comm., vol. 154, No. 3, 1988, pp. 868–875.

Feb, vol. 231, No. 2, 440–444, Apr. 1988 Nature, vol. 332, Mar. 31, 1988.

*Primary Examiner*—Robert T. Bond
*Attorney, Agent, or Firm*—Keil & Weinkauf

[57] ABSTRACT

The description relates to bicyclene derivatives of formula (I) in which A, B, D, E, G, K, L, $R^1$, $R^2$, $Z^1$ and $Z^2$ have the meanings given in the description, and their production. These compounds are suitable for treating diseases.

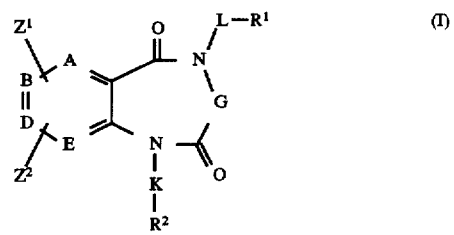

4 Claims, No Drawings

BICYCLE DERIVATIVES, THEIR PREPARATION AND USE

This application is a 371 of PCT/EP 94/03980, filed 30 Nov. 1994 which claims priority of German application P 43 41 6659 filed Dec. 7, 1993.

The present invention relates to novel bicycle derivatives, their preparation and use in therapy.

Endothelin is a peptide which is composed of 21 amino acids and is synthesized and released by the vascular endothelium. Endothelin exists in three isoforms, ET-1, ET-2 and ET-3. "Endothelin" or "ET" hereinafter means one or all isoforms of endothelin. Endothelin is a potent vasoconstrictor and has a powerful effect on vascular tone. It is known that this vasoconstriction is caused by the binding of endothelin to its receptor (Nature, 332, 411≧415, 1988; FEBS Letters, 231, 440–444, 1988 and Biochem. Biophys. Res. Commun., 154, 868–875, 1988).

Elevated or abnormal release of endothelin causes persistent vasoconstriction in peripheral, renal and cerebral blood vessels, which may lead to disorders. It has been reported in the literature that elevated endothelin levels have been found in the plasma of patients with hypertension, acute myocardial infarct, pulmonary hypertension, Raynaud's syndrome, atherosclerosis and in the airways of asthmatics (Japan J. Hypertension, 12, 79 (1989), J. Vascular Med. Biology 2, 207 (1990), J. Am. Med. Association 264, 2868 (1990)).

Accordingly, substances which specifically inhibit the binding of endothelin to the receptor ought also to antagonize the various abovementioned physiological effects of endothelin and therefore represent valuable drugs.

We have found that certain bicycle derivatives have good endothelin-antagonistic activity.

The invention relates to bicycle derivatives of the formula I

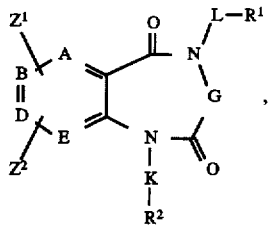

where 2 of the radicals A, B, D and E are CH groups and the 2 other radicals are CH groups or nitrogen atoms, $Z^1$ is hydrogen or halogen, $C_{1-6}$-alkyl, or phenyl, phenyl-$C_{1-4}$-alkyl, naphthyl or naphthyl-$C_{1-6}$-alkyl which is unsubstituted or substituted on the aromatic radical by $C_{1-6}$-alkyl, $C_{1-6}$-alkoxy, halogen, $CF_3$, $NO_2$ or CN, or $C_{2-6}$-alkenyl or $C_{2-6}$-alkynyl, $C_{3-7}$-cycloalkyl or one of the groups —$NHR^4$, —$NR^4{}_2$, —$OR^4$, —$SO_2NHR^4$, —$SO_2NR^4{}_2$, —$COR^4$ or —$CO_2R^4$ (with $R^4$ meaning $C_{1-4}$-alkyl, phenyl, phenyl-$C_{1-4}$-alkyl, naphthyl or naphthyl-$C_{1-4}$-alkyl), $Z^2$ has one of the meanings indicated for $Z^1$ but is not hydrogen, or $Z^1$ and $Z^2$ together with B and D are also one of the radicals

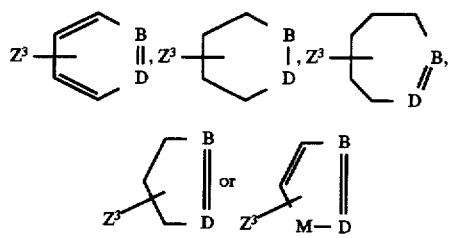

(where $Z^3$ has one of the meanings indicated for $Z^1$, and M is a $CH_2$ or NH group), G is a direct linkage or the group CH—K (with K meaning hydrogen, $C_{1-6}$-alkyl, or a phenyl, benzyl, naphthyl or naphthylmethyl group which is unsubstituted or substituted in the aryl moiety by $C_{1-4}$-alkyl, $C_{1-4}$-alkoxy, halogen, $CF_3$, $NO_2$ or CN), K is alkyl or alkenyl with, in each case, up to 6 C atoms or the group

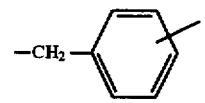

L is an alkylene, alkenylene or alkynylene group with, in each case, up to 6 C atoms or one of the groups

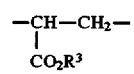

(with $R^3$ meaning hydrogen, $C_{1-4}$-alkyl, benzyl or naphthylmethyl),

(with Q meaning $C_{1-6}$-alkyl, aryl or $CH_2$—$R^7$ where $R^7$ is phenyl or hetaryl) or

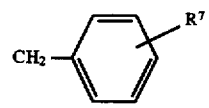

$R^1$ is —$CO_2R^4$ (with $R^4$ meaning hydrogen, $C_{1-4}$-alkyl or benzyl), —$CONR^4{}_2$, —$OR^4$, —$SR^4$, —$SO_3R^4$, —$PO_3R^4{}_2$ or tetrazolyl, and $R^2$ is

(with $R^5$ and $R^6$ meaning hydrogen, $C_{1-4}$-alkyl, —$OR^4$ or —$SR^4$) or hetaryl, and, where appropriate, the salts thereof with physiologically tolerated acids.

Preferred compounds of the formula I are those where one or more of the moieties A, B, D, E, G, K, L, $R^1$, $R^2$, $Z^1$ and $Z^2$ have the following meanings:

A,B,D —CH—

E —CH—, —N—

G —CH₂— or a direct linkage between N and CO

K —CH₂—

L —(CH₂)₁₋₄, 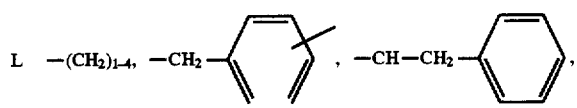

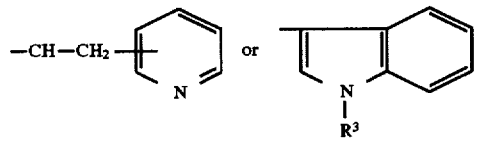

R¹ —COOH

R² 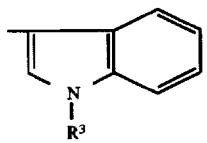

(R³=H, C₁₋₃-alkyl, —CHO, —COO—C₁₋₃-alkyl),

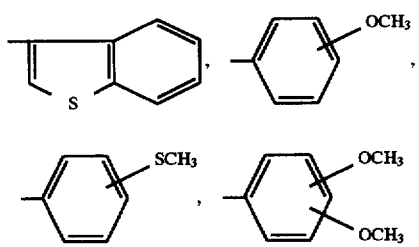

$Z^1$ C₁₋₆-alkyl, C₂₋₆-alkenyl, C₂₋₆-alkynyl, —NH—CO—C₂₋₅-alkyl $Z^2$ hydrogen $Z^1$ and $Z^2$ a radical

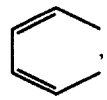

which is linked to B and D and is substituted by one of the radicals mentioned as preferred for $Z^1$.

The compounds of the formula I are obtained, if E is nitrogen, by the following route:

Reaction of a substituted amino carboxylic derivative of the formula II with an amine of the formula III results firstly in IV. Ring closure with an activated derivative of carbonic acid affords the compounds of the formula V. Alkylation of the amide nitrogen leads to the compounds of the formula I. The protective groups which are required where appropriate on the intermediates in the individual reaction steps are introduced and eliminated again by conventional methods.

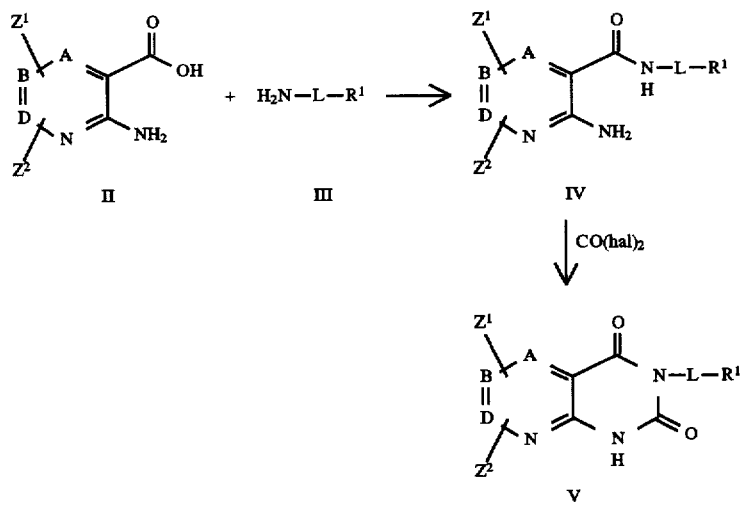

The compounds of the general formula I are obtained, if E is methine or substituted methine, by the following route: The carboxylic acid derivatives of the formula IV are converted into the N-acyl derivative VII by reaction with an activated halo carboxylic acid derivative of the formula VI. The activated halo carboxylic acid derivatives which are preferably used are the corresponding acid halides. Cyclization is then carried out to give VIII with elimination of hydrogen halide. Substitution on the amide nitrogen leads to the compounds of the formula I. The protective groups which are required on the intermediates in the individual reaction steps are introduced and eliminated again by conventional methods.

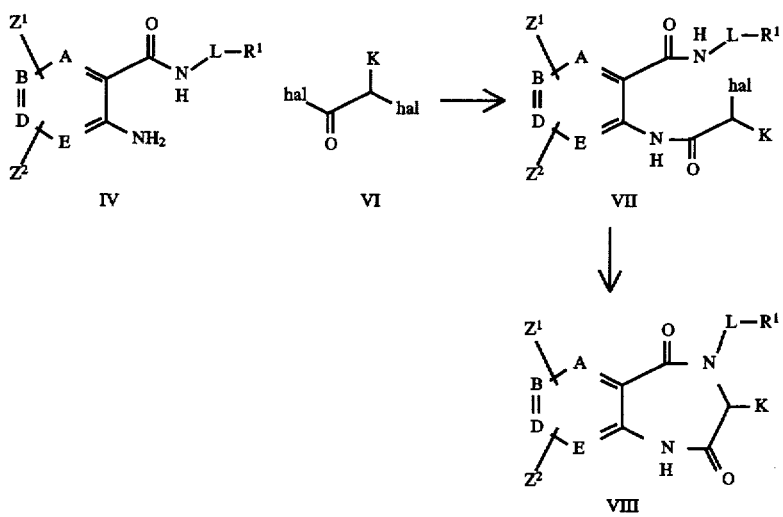

The compounds of the present invention provide a novel therapeutic potential for the treatment of hypertension, pulmonary hypertension, myocardial infarct, angina pectoris, acute kidney failure, renal insufficiency, cerebral vasospasms, cerebral ischemia, subarachnoid hemorrhages, migrane, asthma, atherosclerosis, endotoxic shock, endotoxin-induced organ failure, intravascular coagulation, restenosis after angioplasty and cyclosporin-induced kidney failure, and hypertension.

The good effect of the compounds can be shown in the following experiments:

Receptor Binding Studies

For binding studies, cloned human $ET_A$ receptor-expressing CHO cells and guinea pig cerebellar membranes with >60% $ET_B$ compared with $ET_A$ receptors were used.

Membrane Preparation

The $ET_A$ receptor-expressing CHO cells were grown in $F_{12}$ medium with 10% fetal calf serum, 1% glutamine, 100 U/ml penicillin and 0.2% streptomycin (Gibco BRL, Gaithersburg, Md., USA). After 48 h, the cells were washed with PBS and incubated with 0.05% trypsin-containing PBS for 5 min. Neutralization was then carried out with $F_{12}$ medium, and the cells were collected by centrifugation at 300×g. For lysis of these cells, the pellet was briefly washed with lysis buffer (5 mM Tris-HCl, pH 7.4 with 10% glycerol) and then incubated in a concentration of $10^7$ cells/ml of lysis buffer at 4° C. for 30 min. The membranes were centrifuged at 20,000×g for 10 min, and the pellet was stored in liquid nitrogen.

Guinea pig cerebella were homogenized in a Potter-Elvejhem homogenizer and obtained by differential centrifugation at 1,000×g for 10 min and renewed centrifugation of the supernatant at 20,000×g for 10 min.

Binding Assays

For the $ET_A$ and $ET_B$ receptor binding assay, the membranes were suspended in incubation buffer (50 mM Tris-HCl, pH 7.4 with 5 mM $MnCl_2$, 40 μg/ml bacitracin and 0.2% BSA) at a concentration of 50 μg of protein per assay mixture and incubated at 25° C. with 25 pM [$^{125}$I]-$ET_1$ ($ET_A$ receptor assay) or 25 pM [$^{125}$I]-$RZ_3$ ($ET_B$ receptor assay) in the presence and absence of test substance. The nonspecific binding was determined with $10^{-7}$ M $ET_1$. After 30 min, the free and the bound radioligand were separated by filtration through GF/B glass fiber filters (Whatman, England) on a Skatron cell collector (Skatron, Lier, Norway), and the filters were washed with ice-cold Tris-HCl buffer, pH 7.4 with 0.2% BSA. The radioactivity collected on the filters was quantified using a Packard 2200 CA liquid scintillation counter.

The $K_i$ values were determined by a non-linear regression analysis with the LIGAND program.

Functional in vitro assay system to search for endothelin receptor (subtype A) antagonists.

This assay system is a functional, cell-based assay for endothelin receptors. Certain cells show an increase in the intracellular calcium concentration when they are stimulated with endothelin 1 (ET1). This increase can be measured in intact cells which have been loaded with calcium-sensitive dyes.

1-fibroblasts which had been isolated from rats and on which an endogenous endothelin receptor of subtype A had been detected were loaded with the fluorescent dye Fura 2-an as follows: After trypsinization, the cells were resuspended in buffer A (120 mM NaCl, 5 mM KCl, 1.5 mM $MgCl_2$, 1 mM $CaCl_2$, 25 mM HEPES, 10 mM glucose, pH 7.4) to a density of $2 \times 10^6$/ml and incubated with Fura 2-an (2 μM), Pluronic F-127 (0.04%) and DMSO (0.2%) in the dark at 37° C. for 30 min. The cells were then washed twice with buffer A and resuspended at $2 \times 10^6$/ml.

The fluorescence signal from $2 \times 10^5$ cells per ml with Ex/Em 380/510 was recorded continuously at 30° C. The test substances and then, after incubation for 3 min, ET1 were added to the cells, and the maximum change in fluorescence was determined. The response of the cells to ET1 without previous addition of a test substance served as control and was set equal to 100%.

Testing of ET Antagonists In Vivo

Male SD rats weighing 250–300 g were anaesthetized with amobarbital, artificially ventilated, vagotomized and pithed. The carotid artery and jugular vein were catheterized.

In control animals, intravenous administration of 1 μg/kg of ET1 leads to a distinct rise in blood pressure, which persists for a lengthy period.

The test animals received i.v. injection (1 ml/kg) of the test compounds 5 min before administration of ET1. To determine the ET-antagonistic properties, the rise in blood pressure in the test animals was compared with that in the control animals.

Endothelin-1—Induced Sudden Death in Mice

The principle of the test comprises the inhibition of the sudden heart death caused by endothelin in mice, probably owing to constriction of the coronary vessels, by pretreatment with endothelin receptor antagonists. Intravenous injection of 10 nmol/kg endothelin in a volume of 5 ml/kg of body weight results in death of the animals within a few minutes.

The lethal endothelin-1 dose is checked in each case on a small group of animals. If the test substance is administered intravenously, the lethal endothelin-1 injection in the reference group usually takes place 5 min thereafter. With other modes of administration, the predosage times are longer, where appropriate up to several hours.

The survival rate is recorded and effective doses which protect 50% of the animals against endothelin-induced heart death for 24 h or longer (ED 50) are determined.

Functional Vessel Test for Endothelin Receptor Antagonists

Segments of rabbit aorta under an initial tension of 2 g after a relaxation time of 1 h in Krebs-Henseleit solution at 37° C. and a pH of from 7.3 to 7.4 are initially induced to contract with $K^+$. After washing out, an endothelin dose-effect plot is constructed up to the maximum.

Potential endothelin antagonists are administered to other preparations of the same vessel 15 min before starting the endothelin dose-effect plot. The effects of the endothelin are calculated as a % of the $K^+$-induced contraction. Effective endothelin antagonists shift the endothelin dose-effect plot to the right.

The novel compounds may have acidic or basic groups and may therefore exist in the form of salts.

Particularly suitable physiologically tolerated acids for salt formation are: hydrochloric acid, hydroiodic acid, sulfuric acid, phosphoric acid, acetic acid, citric acid, malonic acid, salicylic acid, maleic acid, fumaric acid, succinic acid, ascorbic acid, malic acid, methanesulfonic acid, lactic acid, gluconic acid, glucuronic acid, sulfamic acid, benzoic acid, tartaric acid.

Examples of suitable bases are alkali metal and alkaline earth metal hydroxides.

The compounds according to the invention can be administered orally or parenterally (subcutaneously, intravenously, intramuscularly, intraperitoneally) in a conventional way. Administration can also take place with vapors or sprays through the nasal pharyngeal space.

The dosage depends on the age, condition and weight of the patient and on the mode of administration. As a rule, the daily dose of active substance is about 0.5–50 mg/kg of body weight on oral administration and about 0.1–10 mg/kg of body weight on parenteral administration.

The novel compounds can be used in conventional solid or liquid pharmaceutical forms, eg. as uncoated or (film-) coated tablets, capsules, powders, granules, suppositories, solutions, ointments, creams or sprays. These are produced in a conventional manner. The active substances can in these cases be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of active substance.

EXAMPLE 1 a) 5-Iodoisatoic anhydride 10 g (0.038 mol) of 5-iodoanthranilic acid were dissolved in 180 ml of THF, and 3.76 g (0.0127 mol) of bis (trichloromethyl) carbonate dissolved in 20 ml of THF were added. The mixture was then stirred at room temperature for 1 h and at 50° C. for 2 h. After cooling, the precipitate was filtered off with suction and dried. 7.8 g (71%) of 5-iodoisatoic anhydride were obtained as white crystals.

b) 2-Amino-5-iodo-N-(2-methoxycarbonylethyl)benzamide 7.28 g (25.2 mmol) of 5-iodoisatoic anhydride and 3.52 g (25.2 mmol) of β-alanine methyl ester hydrochloride were introduced into 60 ml of DMF, and 6.12 g (60.5 mmol) of triethylamine were added dropwise. The mixture was heated at 50° C. for 4 h, cooled and added to a mixture of 15 ml of 2N NaOH with ice. The aqueous phase was extracted with ethyl acetate, and the organic phase was dried and concentrated under reduced pressure. 6.6 g of a yellow oil were obtained and were purified by chromatography on silica gel with ethyl acetate/n-heptane (1:1). 4.6 g (52%) of 2-amino-5-iodo-N-(2-methoxycarbonylethyl)benzamide were obtained with an RF of 0.40 (ethyl acetate/n-heptane, 2:1).

c) 6-Iodo-3-(2-methoxycarbonylethyl)quinazoline-2,4-dione 4.6 g of 2-amino-5-iodo-N-(2-methoxycarbonylethyl) benzamide were introduced with 2.66 g (26.3 mmol) of triethylamine into 50 ml of dichloromethane and, under nitrogen, 1.21 g (4.1 mmol) of bis(trichloromethyl) carbonate dissolved in 15 ml of dichloromethane were added dropwise. The mixture was refluxed for 2 h and, after cooling, added to ice-water. The aqueous phase was extracted with dichloromethane, and the organic phase was dried and concentrated. 3.64 g (74%) of 6-iodo-3-(2-methoxycarbonylethyl)quinazoline-2,4-dione [$R_F$ 0.52 (ethyl acetate/n-heptane, 2:1)] were obtained as a yellowish solid.

d) 6-Iodo-3-(2-methoxycarbonylethyl)-1-(N-t-butylcarbamoyl-3-indolylmethyl)quinazoline-2,4-dione 2.6 g (7 mmol) of 6-iodo-3-(2-methoxycarbonylethyl) quinazoline-2,4-dione and 1.95 g (14.1 mmol) of potassium carbonate were suspended in acetone. To this mixture were added 3.05 g (9.8 mmol) of N-t-butylcarbamoyl-3-indolylmethyl bromide dissolved in 20 ml of acetone, and the mixture was stirred at room temperature for 5 h. The solvent was then stripped off under reduced pressure, and the residue was taken up in 50 ml of phosphate buffer (pH 7) and 150 ml of ethyl acetate. The product was extracted with ethyl acetate, dried and concentrated under reduced pressure. 5.9 g of a dark oil were obtained and were chromatographed on silica gel with ethyl acetate/n-heptane (ratio 1:4) as eluent. 1.9 g (45%) of 6-iodo-3-(2-methoxycarbonylethyl)-1-(N-t-butylcarbamoyl-3-indolylmethyl)quinazoline-2,4-dione, $R_F$ 0.18 (ethyl acetate/n-heptane, 1:4) were obtained.

e) 6-(1-Pentenyl)-3-(2-methoxycarbonylethyl)-1-(N-t-butylcarbamoyl-3-indolylmethyl)quinazoline-2,4-dione 1.09 g (1.8 mmol) of 6-iodo-3-(2-methoxycarbonylethyl)-1-(N-t-butylcarbamoyl-3-indolylmethyl)quinazoline-2,4-dione and 0.75 g (5.4 mmol) of potassium carbonate were introduced in 15 ml of DMF, and 0.63 g (9.0 mmol) of 1-pentene, 0.58 g (1.8 mmol) of tetrabutylammonium bromide and 10 mg of palladium acetate were added. The mixture was stirred at room temperature for 48 h and then concentrated under reduced pressure. The crude product was chromatographed on silica gel, eluent dichloromethane (2% methanol). 0.69 g (70%) of product, $R_F$ 0.12 (dichloromethane+2% methanol) was obtained.

f) 6-(1-Pentenyl)-3-(2-methoxycarbonylethyl)-1-(3-indolylmethyl)quinazoline-2,4-dione 0.53 g of the product obtained in e) was dissolved in 5 ml of dichloromethane, 1.13 g (9.9 mol) of trifluoroacetic acid were added, and the mixture was stirred at room temperature for 16 h. It was then washed with water, dried and concentrated. 0.45 g of crude product was obtained and was reacted further without purification.

g) 6-(1-Pentenyl)-3-(2-carboxyethyl)-1-(3-indolylmethyl)quinazoline-2,4-dione 0.45 g of the crude product obtained in f) was dissolved in 10 ml of THF, and 0.03 mg (1.25 mmol) of lithium hydroxide dissolved in 2 ml of water was added, and the mixture was stirred at room temperature for 16 h. The solvent was stripped off under reduced pressure, and the residue was taken up in ethyl acetate and water; the aqueous phase was adjusted to pH 9 with ammonia solution and extracted with ethyl acetate. The organic phase was dried and concentrated. 0.37 g of crude product was obtained. HPLC (reversed phase material, acetonitrile/water) resulted in 0.12 g (0.28 mmol) of 6-(1-pentenyl)-3-(2-carboxyethyl)-1-(3-indolylmethyl)quinazoline-2,4-dione.

The following were prepared as in Example 1:

6-[E-(3-methyl-1-butenyl)]-3-(2-carboxyethyl)-1-(3-indolylmethyl)quinazoline-2,4-dione 6-[E-(2-[p-(1,1-dimethylethyl)phenyl)]ethenyl-3-(2-carboxyethyl)-1-(3-indolylmethyl)quinazoline-2,4-dione 6-[E-(4-methyl-1-pentenyl)]-3-(2-carboxyethyl)-1-(3-indolylmethyl)quinazoline-2,4-dione 6-[E-(2-cyclohexylethenyl)]-3-(2-carboxyethyl)-1-(3-indolylmethyl)quinazoline-2,4-dione, melting point 122°–126° C.

6-[E-(1-pentenyl)]-3-(carboxymethyl)-1-(N-methyl-3-indolylmethyl)quinazoline-2,4-dione, melting point >300° C.

6-[E-(4-methyl-1-pentenyl)]-3-(carboxymethyl)-1-(N-methyl-3-indolylmethyl)quinazoline-2,4-dione, melting point >300° C.

6-[E-(3,3-dimethyl-1-butenyl)]-3-(carboxymethyl)-1-(N-methyl-3-indolylmethyl)quinazoline-2,4-dione, melting point >300° C.

EXAMPLE 2 a) 6-Iodo-3-(methoxycarbonylmethyl)-1-(N-methyl-3-indolyl)quinazoline-2,4-dione 12.0 g (33.3 mmol) of 6-iodo-3-(methoxycarbonylmethyl)quinazoline-2,4-dione prepared as in Example 1a)–c) were suspended in 250 ml of DMF, and 0.2 g (66.6 mmol) of potassium carbonate was added. Then 16.5 g (49.9 mmol) of (N-methyl-3-indolylmethyl)trimethylammoniumiodide were added and the mixture was refluxed for 6 h. The solvent was stripped off under reduced pressure and then water and ethyl acetate were added, and the product was filtered off with suction and dried. 16.2 g (96.5%) of product were obtained, $R_F$ 0.6 (ethyl acetate/n-heptane, 2:1).

b) 6-(1-Pentenyl)-3-(methoxycarbonylmethyl)-1-(N-methyl-3-indolyl)quinazoline-2,4-dione 2.5 g (4.97 mmol) of the product obtained in a) were introduced into 20 ml of DMF, and 1.46 g (14.9 mmol) of potassium acetate, 1.74 g (24.8 mmol) of 1-pentene, 1.6 g (4.97 mmol) of tetrabutylammonium bromide and 28 mg of palladium(II) acetate were added. The mixture was stirred at room temperature for 16 h. The solvent was stripped off under reduced pressure, and the residue was taken up in ethyl acetate and 10% strength EDTA solution. The organic phase was washed once more with EDTA solution, dried and concentrated. The dark oily residue was chromatographed on silica with ethyl acetate/n-heptane (1:5) as eluent. 1.23 g (55.5%) of product were obtained, $R_F$ 0.61 (ethyl acetate/n-heptane, 1:1).

c) 6-Pentyl-3-(methoxycarbonylmethyl)-1-(N-methyl-3-indolyl)quinazoline-2,4-dione 0.2 g (0.45 mmol) of the product obtained in b) was dissolved in ethyl acetate. After addition of 0.1 g of palladium/active carbon (10% Pd), the mixture was stirred under a hydrogen atmosphere for 6 h, during which 15 ml of hydrogen were consumed. The catalyst was filtered off through silica gel, and the solution was washed with water, dried and concentrated. 0.2 g of a pale yellow solid was obtained and was processed further as the crude product.

d) 6-Pentyl-3-(carboxymethyl)-1-(N-methyl-3-indolyl)quinazoline-2,4-dione 0.2 g (0.45 mmol) of the product obtained in c) was hydrolyzed with lithium hydroxide by the method of Example 1g. 0.11 g of product was obtained, $R_F$ 0.40 (dichloromethane, 20% methanol).

EXAMPLE 3 a) 6-(2-Phenylethynyl)-3-(methoxycarbonylmethyl)-1-(N-methyl-3-indolyl)quinazoline-2,4-dione 3.5 g (6.95 mmol) of 6-iodo-3-(methoxycarbonylmethyl)-1-(N-methyl-3-indolyl)quinazoline-2,4-dione were dissolved in 50 ml of ethyl acetate and 1.42 g (13.9 mmol) of phenylacetylene, 0.49 g (0.65 mmol) of bis(triphenylphosphine)palladium dichloride, 0.066 g of copper (I) iodide and 3.52 g (34.8 mmol) of triethylamine were added. The reaction mixture was refluxed for 8 h. Then 50 ml of ethyl acetate were added. Washing with 10% strength EDTA solution was followed by drying and concentration. The solid brown residue was chromatographed on silica gel with n-heptane/ethyl acetate (4:1) as eluent. 2.76 g (86%) of product were obtained, RF 0.19 (n-heptane/ethyl acetate, 2:1).

b) 6-(2-Phenylethynyl)-3-(carboxymethyl)-1-(N-methyl-3-indolyl)quinazoline-2,4-dione 1.5 g (3.25 mmol) of the product obtained in a) were reacted with 0.12 g (5.0 mmol) of lithium hydroxide as in Example 1g). The product was insoluble in water and ethyl acetate and was filtered off with suction and dried. 0.78 g (52%) of product was obtained, RF 0.72 (n-heptane/ethyl acetate, 1:2), melting point >300° C.

The following were prepared in a similar way:

6-(1-pentynyl)-3-(carboxymethyl)-1-(N-methyl-3-indolyl)quinazoline-2,4-dione

The following can be prepared in a similar way:

6-(4-methyl-1-pentynyl)-3-(carboxymethyl)-1-(N-methyl-3-indolyl)quinazoline-2,4-dione 6-(4-methyl-1-pentynyl)-3-(2-carboxyethyl)-1-(N-methyl-3-indolyl)quinazoline-2,4-dione 6-(4-methyl-1-pentynyl)-3-(3-carboxypropyl)-1-(N-methyl-3-indolyl)quinazoline-2,4-dione

EXAMPLE 4 a) 3-(2-Methylpropoxy)-6-nitrobenzaldehyde 50 g (0.308 mol) of 3-hydroxy-6-nitrobenzaldehyde and 49.3 g (0.36 mol) of 2-methylpropyl bromide were dissolved in 300 ml of DMF, and 45.5 g (0.33 mol) of potassium carbonate were added. The mixture was refluxed for 5 h. After cooling, the solvent was stripped off under reduced pressure, and the residue was dissolved in ethyl acetate and washed with 10% strength sodium carbonate solution and brine. The residue after drying and concentration was chromatographed on silica gel with n-heptane/ethyl acetate (9:1). 55.2 g (80%) of orange crystals were obtained, $R_f$ 0.43 (n-heptane/ethyl acetate, 9:1).

b) 3-(2-Methylpropoxy)-6-nitrobenzoic acid 24.2 g (0.067 mol) of t-butylammoniumpermanganate dissolved in 100 ml of pyridine were added dropwise to a cooled solution of 22.3 g (0.10 mol) of the product obtained in a) in 150 ml of pyridine at such a rate that the temperature did not rise above 20° C. The mixture was stirred at room temperature for 16 h and then poured into an ice/hydrochloric acid mixture and decolorized with $Na_2S_2O_3$. The aqueous phase was extracted with ethyl acetate, the organic phase was made alkaline with ammonia, and the product was extracted into the aqueous phase. After acidification of the aqueous phase, the product was again extracted with ethyl acetate, dried and concentrated. The product was recrystallized from dichloromethane. 12.0 g (75%) of 3-(2-methylpropoxy)-6-nitrobenzoic acid were obtained.

c) 3-(2-Methylpropoxy)-6-aminobenzoic acid 8.8 g (36.8 mmol) of the product obtained in b) were dissolved in 50 ml of glacial acetic acid and, after addition of 1.5 g of palladium/active carbon (10%), the mixture was stirred under a hydrogen atmosphere for 5 h. The catalyst was filtered off with suction through silica gel, and the solvent was stripped off under reduced pressure. Water was added to the residue, and the product was filtered off with suction, washed with ether and dried. 6.87 g (89%) of solid were obtained, $R_f$ 0.3 (n-heptane/ethyl acetate, 1:1).

d) 3-(2-Methylpropoxy)isatoic anhydride 6.87 g (32.8 mmol) of the product obtained in c) were converted into the isatoic anhydride as in Example 1a). 6.51 g (84%) of crude product were obtained and were further processed without purification.

e) 2-Amino-5-(2-methylpropoxy)-N-(2-methoxycarbonylethyl)benzamide 6.51 g (27.7 mmol) of the product obtained in d) were reacted with β-alanine methyl ester hydrochloride as in Example 1b). The crude product was chromatographed on silica gel with n-heptane/ethyl acetate (2:1). 5.21 g (64%) of product were obtained, $R_f$ 0.2 (n-heptane/ethyl acetate, 1:1).

f) 6-(2-Methylpropoxy)-3-(2-methoxycarbonylethyl)quinazoline-2,4-dione 5.21 g (17.7 mmol) of the product obtained in e) were reacted as in Example 1c). The crude product was chromatographed on silica gel with n-heptane/ethyl acetate (2:1). 3.28 g (58%) of product were obtained, $R_f$ 0.28 (n-heptane/ethyl acetate, 1:1).

g) 6-(2-Methylpropoxy)-3-(2-methoxycarbonylethyl)-1-(3-indolylmethyl)quinazoline-2,4-dione 0.35 g (8.76 mmol) of 60% sodium hydride was suspended in 40 ml of THF, and 2.34 g (7.3 mmol) of the product obtained in f) dissolved in 30 ml of DMF were added dropwise. After 30 min, 2.77 g (8.76 mmol) of freshly prepared (3-indolylmethyl)trimethylammonium iodide dissolved in 40 ml of DMF were added dropwise, and the mixture was stirred at room temperature for 18 h. The residue after the solvent had been stripped off under reduced pressure was taken up in ethyl acetate and washed with 5% strength citric acid solution and water. After drying and concentration, the crude product was chromatographed on silica gel with n-heptane/ethyl acetate (2:1). 1.29 g (39%) of product were obtained, $R_f$ 0.52 (n-heptane/ethyl acetate, 1:1).

h) 6-(2-Methylpropoxy)-3-(2-carboxyethyl)-1-(3-indolylmethyl)quinazoline-2,4-dione 1.23 g (2.7 mmol) of the product obtained in g) were hydrolyzed with lithium hydroxide by the method of Example 1f). The crude product was purified by HPLC with acetonitrile/water. 0.56 g (48%) of product was obtained, melting point 199°–201° C.

The following were prepared in a similar way:

6-(2-methylpropoxy)-3-(3-indolylethyl)-1-(carboxymethyl)quinazoline-2,4-dione
6-(2-methylpropoxy)-3-(3-indolylethyl)-1-(2-carboxyethyl)quinazoline-2,4-dione
6-(2-methylpropoxy)-3-(3-indolylethyl)-1-(3-carboxypropyl)quinazoline-2,4-dione
6-(3-methylbutoxy)-3-(2-carboxyethyl)-1-(3-indolylmethyl)quinazoline-2,4-dione.

The following can be prepared as in Examples 1–3 from the corresponding 4- and 6-iodoisatoic anhydrides:

5-(1-pentenyl)-3-(2-carboxyethyl)-1-(N-methyl-3-indolylmethyl)quinazoline-2,4-dione
5-pentyl-3-(2-carboxyethyl)-1-(N-methyl-3-indolylmethyl)quinazoline-2,4-dione
5-(4-methyl-1-pentenyl)-3-(2-carboxyethyl)-1-(N-methyl-3-indolylmethyl)quinazoline-2,4-dione
5-(4-methylpentyl)-3-(2-carboxyethyl)-1-(N-methyl-3-indolylmethyl)quinazoline-2,4-dione
5-(3-methyl-1-butenyl)-3-(2-carboxyethyl)-1-(N-methyl-3-indolylmethyl)quinazoline-2,4-dione
5-(3-methylbutyl)-3-(2-carboxyethyl)-1-(N-methyl-3-indolylmethyl)quinazoline-2,4-dione
7-(1-pentenyl)-3-(2-carboxyethyl)-1-(N-methyl-3-indolylmethyl)quinazoline-2,4-dione
7-(1-pentyl)-3-(2-carboxyethyl)-1-(N-methyl-3-indolylmethyl)quinazoline-2,4-dione
7-(4-methyl-1-pentenyl)-3-(2-carboxyethyl)-1-(N-methyl-3-indolylmethyl)quinazoline-2,4-dione
7-(3-methyl-1-butenyl)-3-(2-carboxyethyl)-1-(N-methyl-3-indolylmethyl)quinazoline-2,4-dione
7-(3-methylbutyl)-3-(2-carboxyethyl)-1-(N-methyl-3-indolylmethyl)quinazoline-2,4-dione

EXAMPLE 5 a) 3-Iodo-6-(bromoacetylamino)-N-(2-methoxycarbonylethyl)benzamide 21.0 g (60.5 mmol) of 3-iodo-6-amino-N-(2-methoxycarbonylethyl)benzamide prepared as in Example 1b) were dissolved in 270 ml of dichloromethane, and 12.5 ml (90.7 mmol) of triethylamine were added. At −30° C., 7.8 ml (90.7 mmol) of bromoacetyl bromide in 80 ml of dichloromethane were added dropwise. The mixture was stirred at room temperature for 2 h and then washed with 10% strength citric acid solution and sodium bicarbonate solution, dried and concentrated. The product was recrystallized from dichloromethane, resulting in 26.1 g (92%) of pale yellow crystals.

b) 7-Iodo-4-(2-methoxycarbonylethyl)-1,4-benzodiazepine-3,5-dione 7.5 g (16 mmol) of the product obtained in a) were suspended in 100 ml of methanol and slowly added dropwise to a solution of 32 mmol of sodium methanolate in 400 ml of methanol. The mixture was stirred for 20 h and then poured into phosphate buffer (pH 7), the methanol was stripped off under reduced pressure, the aqueous phase was extracted with ethyl acetate, and the organic phase was dried and concentrated. The crude product was chromatographed on silica gel with dichloromethane (+3% methanol). 2.6 g (41%) of product were obtained, $R_F$ 0.49 (dichloromethane, 7% methanol).

c) 7-Iodo-1-(N-methyl-3-indolylmethyl)-4-(2-methoxycarbonylethyl)-1,4-benzodiazepine-3,5-dione 2.6 g (6.6 mmol) of the product obtained in b) were dissolved in 100 ml of DMF, 1.82 g (1.32 mmol) of potassium carbonate were added and then 3.27 g (9.9 mmol) of (N-methyl-3-indolylmethyl)trimethylammonium iodide were added. The mixture was refluxed for 6 h, and then the DMF was stripped off under reduced pressure, and the residue was taken up in water. The aqueous phase was extracted with ethyl acetate, and the organic phase was dried and concentrated. The crude product was chromatographed on silica gel with ethyl acetate/n-heptane (1:1) as eluent. 2.1 g (59%) of product were obtained, $R_F$ 0.57 (dichloromethane, 7% methanol).

d) 7-(1-Pentenyl)-1-(N-methyl-3-indolylmethyl)-4-(2-methoxycarbonylethyl)-1,4-benzodiazepine-3,5-dione 2.1 g (3.9 mmol) of the product obtained in c) and 1.63 g (11.7 mmol) of potassium carbonate were introduced into 40 ml of DMF, and 1.37 g (19.5 mmol) of 1-pentene, 1.26 g (3.9 mmol) of tetrabutylammonium bromide and 20 g of palladium(II) acetate were added. The mixture was stirred at 50° C. for 2 h and at room temperature for 16 h. The solvent was then stripped off under reduced pressure, and the residue was chromatographed on silica gel with dichloromethane (+2% methanol). 1.55 g (3.3 mmol=84%) of product were obtained, $R_F$ 0.65 (dichloromethane, 7% methanol).

e) 7-(1-Pentenyl)-1-(N-methyl-3-indolylmethyl)-4-(2-carboxyethyl)-1,4-benzodiazepine-3,5-dione 0.55 g (1.16 mmol) of the product obtained in d) were hydrolyzed by the method of Example 1g). The crude product was purified by HPLC (reversed phase material, acetonitrile/water). 0.22 g (0.48 mmol=41.4%) of product was obtained.

The following can be prepared in a similar way:

7-(4-methyl-1-pentenyl)-1-(N-methyl-3-indolylmethyl)-4-(2-carboxyethyl)-1,4-benzodiazepine-3,5-dione
7-(3-methyl-1-butenyl)-1-(N-methyl-3-indolylmethyl)-4-(2-carboxyethyl)-1,4-benzodiazepine-3,5-dione
6-(4-methyl-1-pentenyl)-1-(N-methyl-3-indolylmethyl)-4-(2-carboxyethyl)-1,4-benzodiazepine-3,5-dione
6-(3-methyl-1-butenyl)-1-(N-methyl-3-indolylmethyl)-4-(2-carboxyethyl)-1,4-benzodiazepine-3,5-dione
8-(3-methyl-1-butenyl)-1-(N-methyl-3-indolylmethyl)-4-(2-carboxyethyl)-1,4-benzodiazepine-3,5-dione

EXAMPLE 6 a) 7-pentyl-1-(N-methyl-3-indolylmethyl)-4-(2-methoxycarbonylethyl)-1,4-benzodiazepine-3,5-dione 1.0 g (2.1 mmol) of the substance of Example 5d) was hydrogenated as in Example 2b). Chromatography of silica gel with ethyl acetate/n-heptane (1:4) resulted in 0.63 g (63%) of product, $R_F$ 0.53 (ethyl acetate/n-heptane, 1:1).

b) 7-Pentyl-1-(N-methyl-3-indolylmethyl)-4-(2-carboxyethyl)-1,4-benzodiazepine-3,5-dione 0.5 g (1.05 mmol) of the product obtained in a) was hydrolyzed as in Example 1g). The crude product was purified by HPLC (reversed phase material/acetonitrile/water). 0.20 g (0.43 mmol=41%) of product was obtained.

The following can be prepared in a similar way:

7-(3-methylbutyl)-1-(N-methyl-3-indolylmethyl)-4-(2-carboxyethyl)-1,4-benzodiazepine-3,5-dione
7-(3-methylbutyl)-1-(N-methyl-3-indolylmethyl)-4-(3-carboxypropyl)-1,4-benzodiazepine-3,5-dione
6-(3-methylbutyl)-1-(N-methyl-3-indolylmethyl)-4-(2-carboxyethyl)-1,4-benzodiazepine-3,5-dione
8-(3-methylbutyl)-1-(N-methyl-3-indolylmethyl)-4-(2-carboxyethyl)-1,4-benzodiazepine-3,5-dione

We claim:

1. A method for treating a mammal in need of endothelin-antagonistic activity which comprises administering a pharmaceutically acceptable amount of a composition as defined in claim 4 of the formula I

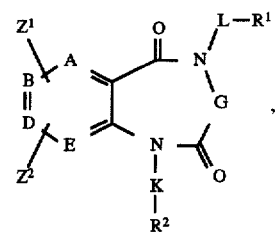

where 2 of the radicals A, B, D and E are CH groups and the 2 other radicals are CH groups or nitrogen atoms, $Z^1$ is hydrogen or halogen, $C_{1-6}$-alkyl, or phenyl, phenyl-$C_{1-4}$-alkyl, naphthyl or naphthyl-$C_{1-6}$-alkyl which are unsubstituted or substituted on the aromatic radical by $C_{1-6}$-alkyl, $C_{1-6}$-alkoxy, halogen, $CF_3$, $NO_2$ or CN, or $C_{2-6}$-alkenyl or $C_{2-6}$-alkynyl, $C_{3-7}$-cycloalkyl or one of the groups —$NHR^4$, —$NR^4_2$, —$OR^4$, —$SO_2NHR^4$, —$SO_2NR^4_2$, —$COR^4$ or —$CO_2R^4$ (with $R^4$ meaning $C_{1-4}$-alkyl, phenyl, phenyl-$C_{1-4}$-alkyl, naphthyl or naphthyl-$C_{1-4}$-alkyl), $Z^2$ has one of the meanings indicated for $Z^1$ but is not hydrogen, or $Z^1$ and $Z^2$ together with B and D are also one of the radicals

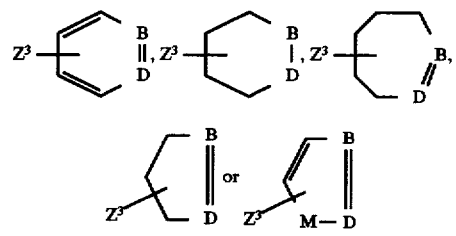

(where $Z^3$ has one of the meanings indicated for $Z^1$, and M is a $CH_2$ or NH group), G is a direct linkage or the group CH—K (with K meaning hydrogen, $C_{1-6}$-alkyl, or a phenyl, benzyl, naphthyl or naphthylmethyl group which is unsubstituted or substituted in the aryl moiety by $C_{1-4}$-alkyl, $C_{1-4}$-alkoxy, halogen, $CF_3$, $NO_2$ or CN), K is alkyl or alkenyl with, in each case, up to 6 C atoms or the group

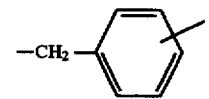

L is an alkylene, alkenylene or alkynylene group with, in each case, up to 6 C atoms or one of the groups $$-\underset{\underset{CO_2R^3}{|}}{CH}-CH_2-$$

(with $R^3$ meaning hydrogen, $C_{1-4}$-alkyl, benzyl or naphthylmethyl), $$-\underset{\underset{CH}{|}}{\overset{\overset{Q}{|}}{CH}}-$$

(with Q meaning $C_{1-6}$-alkyl, aryl or $CH_2-R^7$ where $R^7$ is phenyl or

[indole structure with N-$R^3$]

($R^3$=H, $C_{1-3}$-alkyl, —CHO, —COO—$C_{1-3}$-alkyl)) or

[CH_2-phenyl-$R^7$ structure]

$R^1$ is —$CO_2R^4$ (with $R^4$ meaning hydrogen, $C_{1-4}$-alkyl or benzyl), —$CONR^4{}_2$, —$OR^4$, —$SR^4$, —$SO_3R^4$, —$PO_3R^4{}_2$ or tetrazolyl, and
$R^2$ is

[phenyl structure with $R^5$ and $R^6$ substituents]

(with $R^5$ and $R^6$ meaning hydrogen, $C_{1-4}$-alkyl, —$OR^4$ or —$SR^4$) or hetaryl,
and, where appropriate, the salts thereof with physiologically tolerated acids, for the production of drugs for controlling diseases involving an elevated endothelin level.

2. A compound of the formula I

[Structure Ia]

where
2 of the radicals A, B, D and E are CH groups and the 2 other radicals are CH groups or nitrogen atoms,
$Z^1$ is hydrogen or halogen, $C_{1-6}$-alkyl, or phenyl, phenyl-$C_{1-4}$-alkyl, naphthyl or naphthyl-$C_{1-6}$-alkyl which are unsubstituted or substituted on the aromatic radical by $C_{1-6}$-alkyl, $C_{1-6}$-alkoxy, halogen, $CF_3$, $NO_2$ or CN, or $C_{2-6}$-alkenyl or $C_{2-6}$-alkynyl, $C_{3-7}$-cycloalkyl or one of the groups, —$OR^4$, —$SO_2NHR^4$, —$SO_2NR^4{}_2$, —$COR^4$ or —$CO_2R^4$ (with $R^4$ meaning $C_{1-4}$-alkyl, phenyl, phenyl-$C_{1-4}$-alkyl, naphthyl or naphthyl-$C_{1-4}$-alkyl), $Z^2$ has one of the meanings indicated for $Z^1$ but is not hydrogen, or $Z^1$ and $Z^2$ together with B and D are also one of the radicals

[five cyclic structures with B, D, $Z^3$, M substituents]

(where $Z^3$ has one of the meanings indicated for $Z^1$, and M is a $CH_2$ or NH group), G is a direct linkage or the group CH—K (with K meaning hydrogen, $C_{1-6}$-alkyl, or a phenyl, benzyl, naphthyl or naphthylmethyl group which is unsubstituted or substituted in the aryl moiety by $C_{1-4}$-alkyl, $C_{1-4}$-alkoxy, halogen, $CF_3$, $NO_2$ or CN), K is alkyl or alkenyl with, in each case, up to 6 C atoms or the group

[—$CH_2$-phenyl structure]

L is an alkylene, alkenylene or alkynylene group with, in each case, up to 6 C atoms or one of the groups $$-\underset{\underset{CO_2R^3}{|}}{CH}-CH_2-$$

(with $R^3$ meaning hydrogen, $C_{1-4}$-alkyl, benzyl or naphthylmethyl), $$-\underset{\underset{CH}{|}}{\overset{\overset{Q}{|}}{CH}}-$$

(with Q meaning $C_{1-6}$-alkyl, aryl or $CH_2-R^7$ where $R^7$ is phenyl or

[indole structure with N-$R^3$]

($R^3$=H, $C_{1-3}$-alkyl, —CHO, —COO—$C_{1-3}$-alkyl)) or

[CH_2-phenyl-$R^7$ structure]

$R^1$ is —$CO_2R^4$ (with $R^4$ meaning hydrogen, $C_{1-4}$-alkyl or benzyl), —$CONR^4{}_2$, —$OR^4$, —$SR^4$, —$SO_3R^4$, —$PO_3R^4{}_2$ or tetrazolyl, and $R^2$ is

(with $R^5$ and $R^6$ meaning hydrogen, $C_{1-4}$-alkyl, —$OR^4$ or —$SR^4$) or hetaryl, and, where appropriate, the salts thereof with physiologically tolerated acids.

3. A compound of the formula I

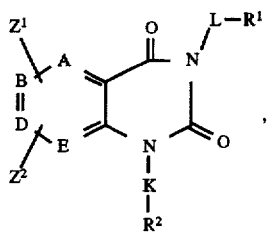

Ib where 2 of the radicals A, B, D and E are CH groups and the 2 other radicals are CH groups or nitrogen atoms, $Z^1$ is hydrogen or halogen, $C_{1-6}$-alkyl, or phenyl, phenyl-$C_{1-4}$-alkyl, naphthyl or naphthyl-$C_{1-6}$-alkyl which are unsubstituted or substituted on the aromatic radical by $C_{1-6}$-alkyl, $C_{1-6}$-alkoxy, halogen, $CF_3$, $NO_2$ or CN, or $C_{2-6}$-alkenyl or $C_{2-6}$-alkynyl, $C_{3-7}$-cycloalkyl or one of the groups —$NHR^4$, —$NR^4_2$, —$OR^4$, —$SO_2NHR^4$, —$SO_2NR^4_2$, —$COR^4$ or —$CO_2R^4$ (with $R^4$ meaning $C_{1-4}$-alkyl, phenyl, phenyl-$C_{1-4}$-alkyl, naphthyl or naphthyl-$C_{1-4}$-alkyl), $Z^2$ has one of the meanings indicated for $Z^1$ but is not hydrogen, or $Z^1$ and $Z^2$ together with B and D are also one of the radicals

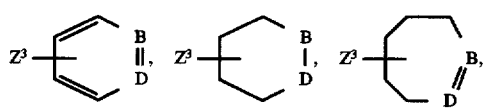

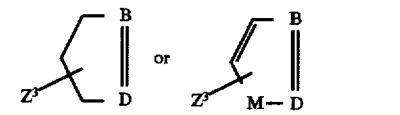

(where $Z^3$ has one of the meanings indicated for $Z^1$, and M is a $CH_2$ or NH group), G is a direct linkage or the group CH—K (with K meaning hydrogen, $C_{1-6}$-alkyl, or a phenyl, benzyl, naphthyl or naphthylmethyl group which is unsubstituted or substituted in the aryl moiety by $C_{1-4}$-alkyl, $C_{1-4}$-alkoxy, halogen, $CF_3$, $NO_2$ or CN), K is alkyl or alkenyl with, in each case, up to 6 C atoms or the group

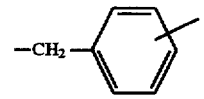

L is

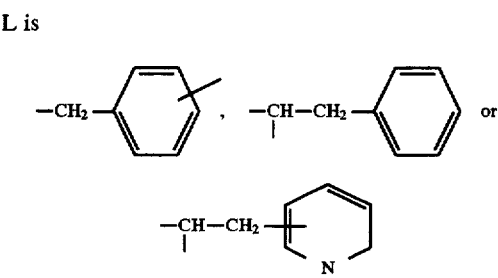

$R^1$ is —$CO_2R^4$ (with $R^4$ meaning hydrogen, $C_{1-4}$-alkyl or benzyl), —$CONR^4_2$, —$OR^4$, —$SR^4$, —$SO_3R^4$, —$PO_3R^4_2$ or tetrazolyl, and $R^2$ is

(with $R^5$ and $R^6$ meaning hydrogen, $C_{1-4}$-alkyl, —$OR^4$ or —$SR^4$) or

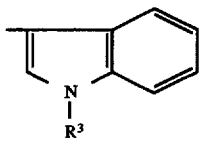

($R^3$=H, $C_{1-3}$-alkyl, —CHO, —COO—$C_{1-3}$-alkyl), and, where appropriate, the salts thereof with physiologically tolerated acids.

4. A pharmaceutical composition comprising a pharmaceutically acceptable excipient and a compound as defined in claim 2.

* * * * *